(12) United States Patent
Kuban et al.

(10) Patent No.: US 7,927,275 B2
(45) Date of Patent: Apr. 19, 2011

(54) SYSTEM AND METHOD OF AQUIRING BLOOD-VESSEL DATA

(75) Inventors: Barry D. Kuban, Avon Lake, OH (US); Jon D. Klingenamith, Shaker Heights, OH (US); D. Geoffrey Vince, Avon Lake, OH (US); Anuja Nair, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1042 days.

(21) Appl. No.: 10/647,977

(22) Filed: Aug. 25, 2003

(65) Prior Publication Data

US 2004/0039286 A1    Feb. 26, 2004

Related U.S. Application Data

(60) Provisional application No. 60/406,183, filed on Aug. 26, 2002, provisional application No. 60/406,254, filed on Aug. 26, 2002, provisional application No. 60/406,148, filed on Aug. 26, 2002, provisional application No. 60/406,184, filed on Aug. 26, 2002, provisional application No. 60/406,185, filed on Aug. 26, 2002, provisional application No. 60/406,234, filed on Aug. 26, 2002.

(51) Int. Cl.
*A61B 8/00* (2006.01)

(52) U.S. Cl. ..................................................... 600/437

(58) Field of Classification Search .................. 600/437, 600/428, 466–468
See application file for complete search history.

(56) References Cited

U.S. PATENT DOCUMENTS 4,228,804 A    10/1980    Holasek
(Continued)

FOREIGN PATENT DOCUMENTS

WO    WO 01/20552 A1    3/2001
(Continued)

OTHER PUBLICATIONS

Bruining et al., Dynamic Three-dimensional Reconstruction of ICUS Images based on an ECG-Gated Pull-Back Device, 1996, 18th Annual international Conference for the IEEE Engineering in Medicine and Biology Society, p. 664-665.*

(Continued)

*Primary Examiner* — Tse Chen
*Assistant Examiner* — Jacqueline Cheng
(74) *Attorney, Agent, or Firm* — Haynes and Boone LLP

(57) ABSTRACT

A system and method is provided for substantially synchronizing the acquisition of blood-vessel data to an identifiable portion of heartbeat data. Specifically, a data-gathering device is adapted to acquire heartbeat data and blood-vessel data from a heart-monitoring device and a data-gathering probe, respectively. In a preferred embodiment of the present invention, the blood-vessel data is acquired during a cyclical portion of the heartbeat data. By identifying a cyclical (or commonly reoccurring) portion of the heartbeat data and acquiring blood-vessel data during this cyclical portion (or during an interval that substantially corresponds thereto), the blood vessel can be analyzed as if it were standing still—i.e., not expanding and relaxing. In one embodiment of the present invention, the heart-monitoring device includes an EKG device, the data-gathering device includes an intra-vascular ultrasound (IVUS) device and a computing device, and the data-gathering probe includes at least one transducer. In another embodiment of the present invention, the data-gathering system further includes a retraction device adapted to move the data-gathering probe though a blood vessel at a substantially steady speed.

41 Claims, 3 Drawing Sheets

U.S. PATENT DOCUMENTS

| | | | |
|---|---|---|---|
| 4,501,279 A * | 2/1985 | Seo | 600/456 |
| 4,511,984 A | 4/1985 | Sumino | |
| 4,561,019 A | 12/1985 | Lizzi | |
| 4,575,799 A | 3/1986 | Miwa | |
| 4,858,124 A | 8/1989 | Lizzi | |
| 4,917,097 A | 4/1990 | Proudian et al. | |
| 4,920,413 A * | 4/1990 | Nakamura et al. | 348/74 |
| 5,161,535 A | 11/1992 | Short | |
| 5,235,984 A | 8/1993 | D'Sa | |
| 5,284,148 A * | 2/1994 | Dias et al. | 600/463 |
| 5,357,550 A | 10/1994 | Asahina | |
| 5,363,850 A | 11/1994 | Soni | |
| 5,417,213 A | 5/1995 | Prince | |
| 5,417,214 A | 5/1995 | Roberts | |
| 5,417,215 A | 5/1995 | Evans | |
| 5,445,155 A | 8/1995 | Sieben | |
| 5,588,432 A | 12/1996 | Crowley | |
| 5,601,085 A | 2/1997 | Ostensen | |
| 5,724,972 A | 3/1998 | Petrofsky | |
| 5,735,281 A | 4/1998 | Rafter | |
| 5,771,895 A * | 6/1998 | Slager | 600/462 |
| 5,846,202 A | 12/1998 | Ramamurthy | |
| 5,876,343 A | 3/1999 | Teo | |
| 5,885,218 A | 3/1999 | Teo | |
| 5,938,607 A | 8/1999 | Jago | |
| 5,957,138 A | 9/1999 | Lin | |
| 5,957,845 A | 9/1999 | Holley | |
| 5,976,088 A | 11/1999 | Urbano | |
| 5,993,390 A | 11/1999 | Savord et al. | |
| 6,004,270 A * | 12/1999 | Urbano et al. | 600/443 |
| 6,050,946 A | 4/2000 | Teo | |
| 6,095,976 A | 8/2000 | Nachotomy | |
| 6,106,460 A | 8/2000 | Panescu | |
| 6,106,465 A | 8/2000 | Napolitano | |
| 6,110,120 A | 8/2000 | Holley | |
| 6,120,445 A | 9/2000 | Grunwald | |
| 6,148,095 A * | 11/2000 | Prause et al. | 382/131 |
| 6,152,878 A | 11/2000 | Nachtomy et al. | |
| 6,200,268 B1 * | 3/2001 | Vince et al. | 600/443 |
| 6,201,900 B1 | 3/2001 | Hossack | |
| 6,216,027 B1 | 4/2001 | Willis | |
| 6,217,517 B1 | 4/2001 | Grunwald | |
| 6,238,342 B1 | 5/2001 | Feleppa | |
| 6,252,924 B1 | 6/2001 | Davantes | |
| 6,254,541 B1 | 7/2001 | Teo | |
| 6,275,560 B1 | 8/2001 | Blake | |
| 6,275,724 B1 | 8/2001 | Dickinson | |
| 6,287,259 B1 | 9/2001 | Grunwald | |
| 6,306,089 B1 | 10/2001 | Coleman | |
| 6,306,095 B1 | 10/2001 | Holley | |
| 6,335,980 B1 | 1/2002 | Armato | |
| 6,360,027 B1 | 3/2002 | Hossack | |
| 6,364,835 B1 * | 4/2002 | Hossack et al. | 600/443 |
| 6,381,350 B1 | 4/2002 | Klingensmith et al. | |
| 6,428,479 B1 | 8/2002 | Aksnes | |
| 6,454,715 B2 | 9/2002 | Teo | |
| 6,490,474 B1 | 12/2002 | Willis | |
| 6,514,202 B2 | 2/2003 | Grunwald | |
| 6,544,187 B2 | 4/2003 | Seward | |
| 6,626,831 B2 | 9/2003 | Holley | |
| 6,673,018 B2 | 1/2004 | Friedman | |
| 6,780,152 B2 | 8/2004 | Ustuner | |
| 6,818,199 B1 | 11/2004 | Hainfeld | |
| 6,845,260 B2 | 1/2005 | Liu | |
| 2001/0007940 A1 * | 7/2001 | Tu et al. | 606/41 |
| 2001/0014774 A1 | 8/2001 | Grunwald | |
| 2003/0028118 A1 | 2/2003 | Dupree | |
| 2003/0045796 A1 | 3/2003 | Friedman | |
| 2003/0092993 A1 | 5/2003 | Grunwald | |
| 2004/0127798 A1 | 7/2004 | Dala-Krishna | |

FOREIGN PATENT DOCUMENTS

| | | |
|---|---|---|
| WO | WO 02/064011 A2 | 8/2002 |

OTHER PUBLICATIONS

Nair, A., Kuban, B., Obuchowski, N., and Vince, D., "Assessing Spectral Algorithms to Predict Atherosclerotic Plaque Composition With Normalized and Raw Intravascular Ultrasound Data", Ultrasound in Medicine and Biology, 2001, pp. 1319-1331, vol. 27, No. 10, Elsevier, U.S.A.

Nair, A., Kuban, B., Tuzcu, E., Schoenhagen, P., Nissen, S., and Vince, D., "Coronary Plaque Classification With Intravascular Ultrasound Radiofrequency Data Analysis", Circulation, 2002, pp. 2200-2206: 106, American Heart Association, U.S.A.

Klingensmith, J. and Vince, D., "B-Spline Methods for Interactive Segmentation and Modeling of Lumen and Vessel Surfaces in Three-Dimensional Intravascular Ultrasound," Computerized Medical Imaging and Graphics 26, 2002, pp. 429-438, Elsevier Science Ltd., U.S.A.

Achenbach, S., Giesler, T., Ropers, D., Ulzheimer, S., Derlien, H., Schulte, C., Wenkel, E., Moshage, W., Bautz, W., Daniel, W., Kalender, W., Baum, U., "Detection of Coronary Artery Stenoses by Contrast-Enhanced, Retrospectively Electrocadiographically-Gated, Multislice Spiral Computed Tomography", Circulation, 2001, pp. 2535-2538, vol. 103, No. 21, American Heart Association, Dallas, U.S.A.

Arbab-Zadeh, A., Demaria, A., Penny, W., Russo, R., Kimura, B., Bhargava, V., "Axial Movement of the Intravascular Ultrasound Probe During the Cardiac Cycle: Implications for Three-Dimensional Reconstruction and Measurements of Coronary Dimensions", American Heart Journal, 1999, pp. 865-872, vol. 138, No. 5 Part 1, Elsevier, St. Louis, U.S.A.

Bruining, N., Von Birgelen, C., De Feyter, P., Ligthart, J., Li, W., Serruys, P., Roelandt, J., "ECG-Gated Versus Nongated Three-Dimensional Intracoronary Ultrasound Analysis: Implications for Volumetric Measurements", Catheterization and Cardiovascular Diagnosis, 1998, pp. 254-260, vol. 43, No. 3, Alan R. Liss Inc., New York, U.S.A.

Bruining, N., Von Birgelen, C., De Feyter, P., Ligthart, J., Serruys, P., Roelandt, J., "Dynamic Imaging of Coronary Stent Structures: An ECG-Gated Three-Dimensional Intracoronary Ultrasound Study In Humans", Ultrasound in Medicine and Biology, 1998, pp. 631-637, vol. 24, No. 5, Elsevier, New York, U.S.A.

Delcker, A., Tegeler, C., "Influence of ECG-Triggered Data Acquisition of Reliability for Carotid Plaque Volume Measurements with a Magnetic Sensor Three-Dimensional Ultrasound System", Ultrasound in Medicine and Biology, 1998, pp. 601-605, vol. 24, No. 4, Elsevier, New York, U.S.A.

Søndergaard, L., Ståhlberg, F., Thomsen, C., Spraggins, T., Gymoese, E., Malmgren, L., Müller, E., Henriksen, O., "Comparison Between Retrospective Gating and ECG Triggering in Magnetic Resonance Velocity Mapping", Magnetic Resonance Imaging, 1993; pp. 533-537, vol. 11, No. 4, Pergamon Press, New York, U.S.A.

Stähr, P., Voightländer, T., Rupprecht, H., Aschenbrücker, P., Mamtimin, H, Brennecke, R., Otto, M., Fitzgerald, P., Meyer, J., "Impact of Vessel Curvature on the Accuracy of Three-Dimensional Intravascular Ultrasound: Validation by Phantoms and Coronary Segments", Journal of the American Society of Echocardiography, 2002, pp. 823-830, vol. 15, No. 8, C. V. Mosby, St. Louis, U.S.A.

Von Birgelen, C., De Vrey, E., Mintz, G., Nicosia, A., Bruining, N., Li, W., Slager, C., Roelandt, J., Serruys, P., De Feyter, P., "ECG-Gated Three-Dimensional Intravascular Ultrasound: Feasibility and Reporoducibility of the Automated Analysis of Coronary Lumen and Atherosclerotic Plaque Dimensions in Humans", Circulation, 1997, pp. 2944-2952, vol. 96, No. 9, American Heart Association, Dallas, U.S.A.

Woodhouse, C., Janowitz, W., Viamonte, M., "Coronary Arteries: Retrospective Cardiac Gating Technique to Reduce Cardiac Motion Artifact at Spiral CT", Radiology, 1997, pp. 566-569, vol. 204, No. 2, Radiological Society of North America, Easton, U.S.A.

Supplementary Partial European Search Report for EP 03 79 3358; dated May 8, 2008.

* cited by examiner

SYSTEM AND METHOD OF AQUIRING BLOOD-VESSEL DATA

CROSS-REFERENCE TO RELATED APPLICATION

This application claims the benefit pursuant to 35 U.S.C. §119(e) of U.S. Provisional Patent Application No. 60/406,183, filed Aug. 26, 2002, No. 60/406,254, filed Aug. 26, 2002, No. 60/406,148, filed Aug. 26, 2002, No. 60/406,184, filed Aug. 26, 2002, No. 60/406,185, filed Aug. 26, 2002, and No. 60/406,234, filed Aug. 26, 2002, all of which are incorporated herein, in their entirety, by reference.

BACKGROUND OF THE INVENTION

1. Field of the Invention

The present invention relates to acquiring blood-vessel data, or more particularly, to a system and method of substantially synchronizing the acquisition of blood-vessel data to an identifiable portion of heartbeat data.

2. Description of Related Art

Blood-vessel data (e.g., data that can be used to identify the shape of a blood vessel, its density, its composition, etc.) can provide useful information in the diagnoses and/or treatment of a patient. For example, intra-vascular ultrasound (IVUS) devices use blood-vessel data to reproduce or image a blood vessel. Specifically, a transducer is attached to a distal end of a catheter and electrically connected to an IVUS device. The transducer is then placed inside a particular blood vessel and used to transmit acoustic signals. The reflections of these signals are then received by the transducer, converted into electrical signals, and transmitted to the IVUS device. The electrical signals are then used to create an image of the blood vessel (or a portion thereof).

Blood vessels, however, are continuously expanding and relaxing in response to blood being pumped there through. Thus, by continuously gathering blood-vessel data, a blood vessel, as it expands and relaxes, can be imaged. If, however, the blood vessel needs to be monitored in a particular position (e.g., to image the blood vessel as if it were standing sill—i.e., not expanding and relaxing), it may be necessary to acquire the blood-vessel data when the blood vessel's shape is substantially uniform (i.e., when the blood vessel is in a particular position).

The traditional method of doing this (at least with respect to an IVUS device) is to gather both blood-vessel and heartbeat data (e.g., EKG data), use the blood-vessel data to generate real-time images (i.e., video of the expanding and contracting blood vessel), record these images onto a VHS tape, and use a computer and the heartbeat data to extract relevant frames from the VHS tape. The heartbeat data is used by the computer because the rhythm of the heart is related to the expansion and contraction of the blood vessels. Thus, by extracting the frames recorded during an identifiable period in the heart's cycle, the blood vessel can be monitored as if it were standing still—i.e., not expanding and contracting.

The drawbacks of this method is that image resolution is lost when the data is recorded onto the VHS tape. Furthermore, this method is extremely time consuming. Not only is unnecessary data (i.e., data unrelated to the identifiable period) gathered and recorded onto the VHS tape, but processing time is necessary to extract the relevant frames from the VHS tape. Thus, a need exists for a system and method of acquiring blood-vessel data from a blood vessel in a particular position that overcomes at least one of these drawbacks.

SUMMARY OF THE INVENTION

The present invention provides a system and method of substantially synchronizing the acquisition of blood-vessel data to an identifiable portion of heartbeat data. Preferred embodiments of the present invention operate in accordance with a heart-monitoring device, a data-gathering device, and a data-gathering probe. Specifically, a data-gathering device is adapted to acquire heartbeat data and blood-vessel data from a heart-monitoring device and a data-gathering probe, respectively. In a preferred embodiment of the present invention, the blood-vessel data is acquired during a cyclical portion of the heartbeat data. As previously discussed, it is the contraction and relaxation of the heart muscles (or the blood that flows as a result thereof) that causes the blood vessels to expand and relax. Thus, it is possible to identify a particular position (or shape) of a blood vessel by identifying a corresponding portion of the heart's repetitive cycle. This information (i.e., the identified portion of the heartbeat data) can be used to acquire blood-vessel data (or multiple sets thereof) from a blood vessel having a substantially uniform shape. In other words, by identifying a cyclical (or commonly reoccurring) portion of heartbeat data and acquiring blood-vessel data during this cyclical portion (or during an interval or time period that substantially corresponds thereto), the blood vessel can be analyzed as if it were standing still—i.e., not expanding and relaxing.

In one embodiment of the present invention, the heart-monitoring device includes an EKG device. An EGK device uses a plurality of electrodes to measure electrical current passing through a patient's body. The electrical current corresponds to the electrical activity of the patient's heart muscles, or the contraction and relaxation thereof. This current (or related data) can be used to identify a cyclical portion of the heart's cycle, thus allowing blood-vessel data to be acquired during intervals that substantially correspond thereto (i.e., when the blood vessel is in a substantially uniform position).

In another embodiment of the present invention, the data-gathering device includes an intra-vascular ultrasound (IVUS) device and a computing device. In this embodiment, the IVUS device is adapted to receive blood-vessel data from the data-gathering probe (either continuously or during intervals that substantially correspond to cyclical periods of heartbeat data). The blood-vessel data (or data resulting therefrom) is then acquired by the computing device (e.g., received and/or stored) during intervals that substantially correspond to cyclical periods of heartbeat data.

In another embodiment of the present invention, the data-gathering device includes an IVUS device or a computing device. In this embodiment, blood-vessel data is received and/or stored by the data-gathering device during intervals that substantially correspond to cyclical portions of heartbeat data.

In another embodiment of the present invention, the data-gathering probe includes at least one transducer attached to a distal end of a catheter, where the catheter further includes a data-transmission circuit for transmitting (and receiving) electrical signals to (or from) the transducer(s). In this embodiment, the transducer is placed inside a blood vessel and used to gather blood-vessel data by transmitting and receiving acoustic waves.

In another embodiment of the present invention, the data-gathering system further includes a retraction device. Specifically, the retraction device is attached to the data-gathering probe and used to move the probe though a blood vessel. In one embodiment of the present invention, the retraction device is further adapted to move the probe through the blood vessel at a substantially steady speed.

A more complete understanding of the system and method of substantially synchronizing the acquisition of blood-vessel data to an identifiable portion of heartbeat data will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a system and method of substantially synchronizing the acquisition of blood-vessel data to an identifiable portion of heartbeat data. In the detailed description that follows, like element numerals are used to describe like elements illustrated in one or more figures.

Figure 1:
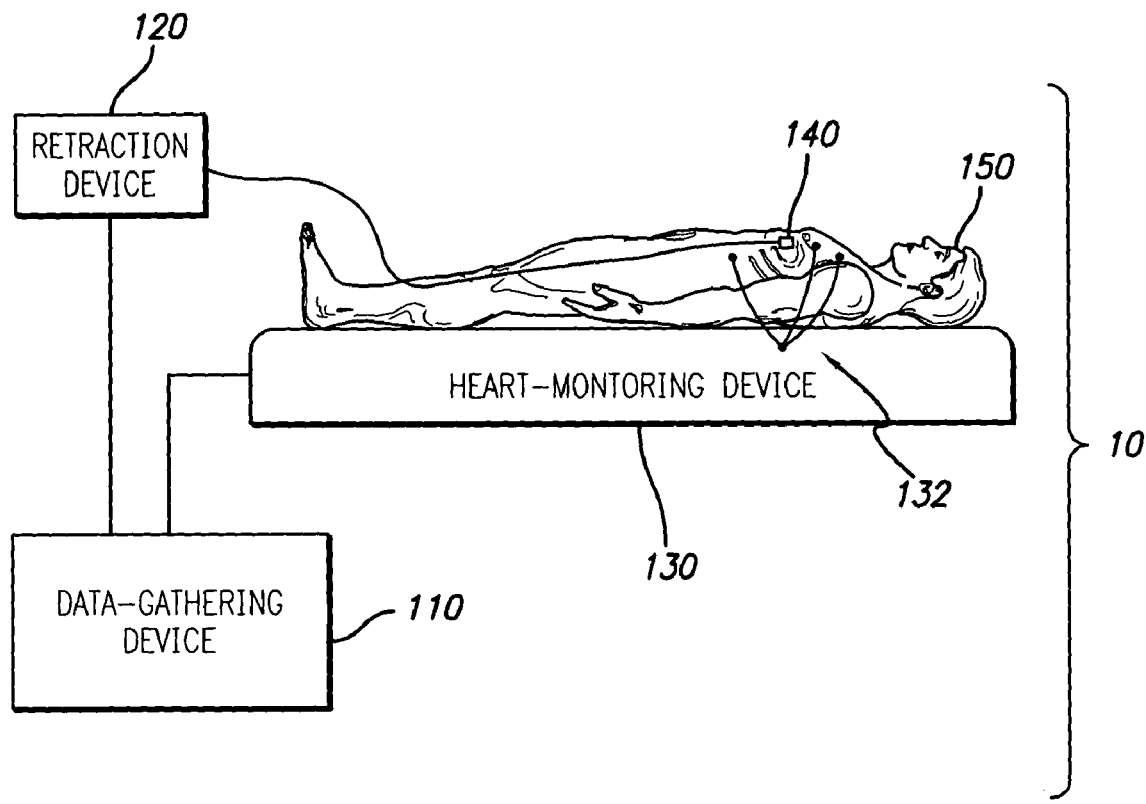
FIG. 1 illustrates a data-gathering system that substantially synchronizes the acquisition of blood-vessel data to an identifiable portion of heartbeat data.

Preferred embodiments of the present invention operate in accordance with a heart-monitoring device, a data-gathering device, and a data-gathering probe. FIG. 1 illustrates a data-gathering system 10 in accordance with one embodiment of the present invention. In this embodiment, a data-gathering device 110 is electrically connected to a heart-monitoring device 130, which is attached to a patient 150 via at least one heart-monitoring probe 132. The heart-monitoring device 130 is used to gather heartbeat data (e.g., data related to the contraction and/or relaxation of the heart muscles, data related to the volume and/or pressure of blood flowing as a result thereof, etc.) from the patient 150. This heartbeat data is then provided to (or acquired by) the data-gathering device 110. It should be appreciated that the data-gathering device depicted in FIG. 1 includes, but is not limited to, ultrasonic devices (e.g., an intravascular ultrasound (IVUS) console), thermographic devices, optical devices (e.g., an optical coherence tomography (OCT) console), MRI devices, computing devices (e.g., a personal computer, a general purpose computing device, an application specific computing device, etc.), and/or any other data gathering devices (including combinations thereof) that are generally known to those skilled in the art. It should further be appreciated that the heart-monitoring device depicted in FIG. 1 includes, but is not limited to, electrocardiograph (EKG) devices, pressure-monitoring devices, or any other heart monitoring device that is generally known to those skilled in the art and can be used to monitor the heart's cycle (or data related thereto—e.g., pressure levels, electrical signals, etc.).

The data-gathering device 110 is further electrically connected to a data-gathering probe 140, which is inserted into a blood vessel (not shown) of the patient 150. The data-gathering probe 140 is used to gather blood-vessel data (e.g., data that can be used to identify the shape of a blood vessel, its density, its composition, etc.). This data (or data related thereto) is then provided to (or acquired by) the data-gathering device 110. It should be appreciated that the data-gathering probe includes, but is not limited to, at least one transducer or any other reception device that is generally known to those skilled in the art. Thus, for example, the use of any reception device adapted to acquire data (e.g., reflected data, etc.), regardless of whether the data is thermal, optical, acoustical, electrical, etc., is within the spirit and scope of the present invention. It should further be appreciated that the number and/or location of components depicted in FIG. 1 are not intended to limit the present invention, but are merely provided to illustrate the environment in which the present invention operates. Thus, for example, a data-gathering system including multiple data-gathering devices, multiple data-gathering probes, and/or additional or fewer components is within the spirit and scope of the present invention.

In a preferred embodiment of the present invention, the blood-vessel data is acquired during a cyclical portion of the heartbeat data. As previously discussed, it is the contraction and relaxation of the heart muscles (or the blood that flows as a result thereof) that causes the blood vessels to expand and relax. Thus, it is possible to identify a particular position (or shape) of a blood vessel by identifying a corresponding portion of the heart's repetitive cycle. This information (i.e., the identified portion of the heartbeat data) can be used to acquire blood-vessel data (or multiple sets thereof) from a blood vessel having a substantially uniform shape. In other words, by identifying a cyclical (or commonly reoccurring) portion of heartbeat data and acquiring blood-vessel data during this cyclical portion (or during an interval or time period that substantially corresponds thereto), the blood vessel can be analyzed as if it were standing still—i.e., not expanding and relaxing. It should be appreciated that the term "acquire" (or any variation thereof), as that term is used herein, should be construed broadly to include the reception and/or storage of data. Thus, for example, a data-gathering device (or a portion thereof) adapted to receive and/or store blood-vessel data (or data related thereto) during a cyclical portion of the heartbeat data is within the spirit and scope of the present invention.

Figure 1A:
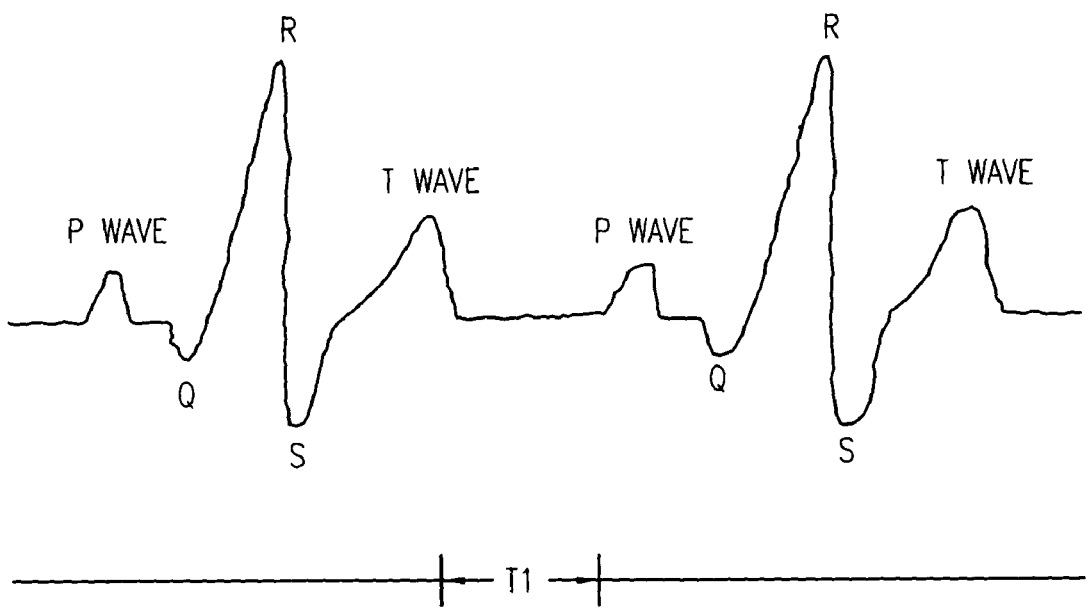
FIG. 1A illustrates an interval (T1) that substantially corresponds to an exemplary cyclical portion of heartbeat data (e.g., EKG data).

In one embodiment of the present invention, the heart-monitoring device includes an EKG device. An EKG device uses a plurality of electrodes to measure electrical current passing through a patient's body. The electrical current corresponds to the electrical activity of the patient's heart muscles, or the contraction and relaxation thereof. By plotting or imaging this current, the heart's rhythm (or cycles) can be observed. An example of such an image (i.e., multiple sets of heartbeat data) is illustrated in FIG. 1A. Specifically, each heart cycle includes a P wave, a T wave, and points Q, R and S. These identifiable portions make it possible to identify a cyclical (or commonly reoccurring) portion of the heart's cycle (or heartbeat data).

For example, the portion between the end of the T wave and the beginning of the P wave can be identified as a cyclical portion of heartbeat data having a corresponding interval T1. This portion, or more particular its interval T1, can be used to acquire blood-vessel data from a uniformly shaped blood vessel. This is because the interval T1 (which reoccurs periodically) substantially corresponds to the identified cyclical portion, which substantially corresponds to a blood vessel having a particular shape or position. It should be appreciated that, while it may be advantageous to identify certain cyclical portions of heartbeat data, the present invention is not limited to the identification of any particular cyclical portion. It should further be appreciated that the term "portion" (or any variation thereof), as that term is used herein, should be construed broadly to include both segments and points of heartbeat data. Furthermore, it should also be appreciated that the terms "interval" and "time period" (or any variations thereof), as these terms are used herein, should be construed broadly to include both passages of time and points in time. Thus, for example, identifying the point "Q" as a cyclical portion of heartbeat data, which has a corresponding interval, or a corresponding point in time (as opposed to a passage of time), is within the spirit and scope of the present invention.

Figure 2:
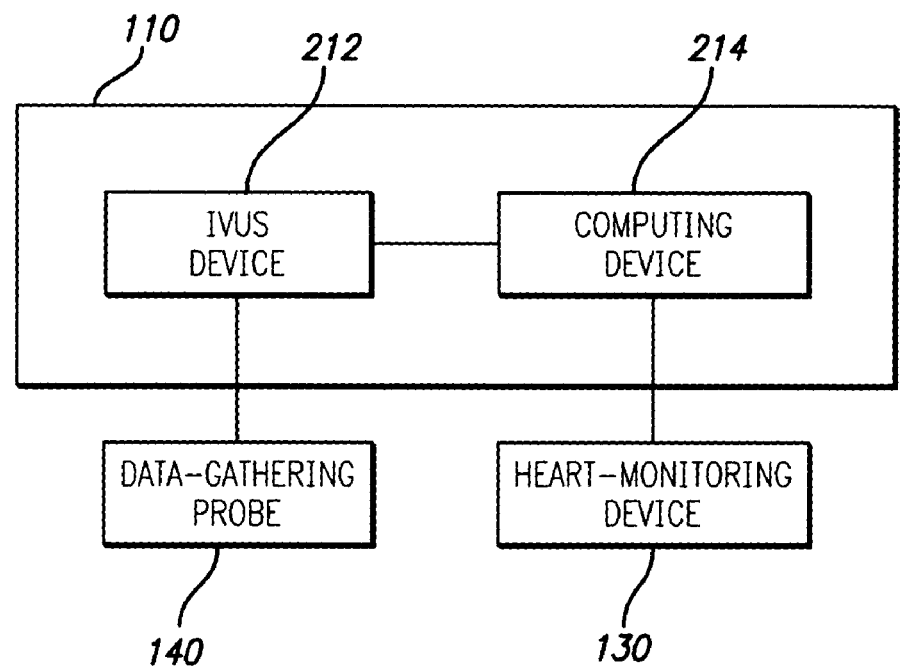
FIG. 2 further illustrates the data-gathering device depicted in FIG. 1.

In one embodiment of the present invention, the data-gathering device includes both an IVUS device and a computing device. Specifically, as shown in FIG. 2, the data-gathering device 110 includes an IVUS device 212 electrically connected to the data-gathering probe 140 and a computing device 214 electrically connected to the heart-monitoring device 130. Thus, the computing device 214 is adapted to acquire (via the IVUS device 212) blood-vessel data (or data related thereto) during intervals that correspond to cyclical portions of heartbeat data. It should be appreciated that the phrase "blood-vessel data," as that phrase is used herein, is to be construed broadly and includes the blood-vessel data gathered by the data-gathering probe and any blood-vessel data related thereto or created therefrom (e.g., as processed by the IVUS device). It should further be appreciated that, in this embodiment, it is the computing device 214 that is adapted to acquire blood-vessel data during intervals that correspond to cyclical portions of heartbeat data. Thus, while the IVUS device may also be adapted to acquire blood-vessel data during these intervals, an IVUS device adapted to continuously receive heartbeat data is within the spirit and scope of the present invention.

Figure 3:
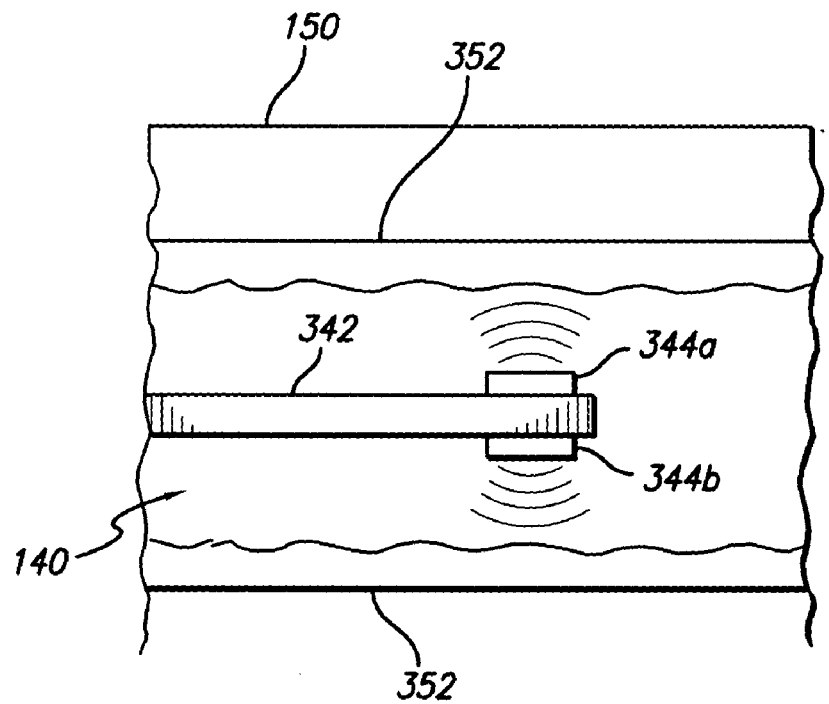
FIG. 3 illustrates a data-gathering probe including a plurality of transducer and located within a blood vessel.

In one embodiment of the present invention, the data-gathering probe includes at least one transducer. Specifically, as shown in FIG. 3, a plurality of transducers 344a, 344b, are attached to a distal end of a catheter 342 having a data-transmission circuit located therein (not shown). In this embodiment, the transducers 344a, 344b are placed inside a blood vessel 352 of the patient 150 and used to gather blood-vessel data. Specifically, each transducer is adapted to (i) convert electrical signals into acoustic waves, (ii) transmit the acoustic waves, (iii) receive any reflections thereof, and (iv) convert the reflections into electrical signals. In this embodiment, the electrical signals are propagated over (i.e., received from and transmitted over) the data-transmission circuit (not shown).

Figure 4:
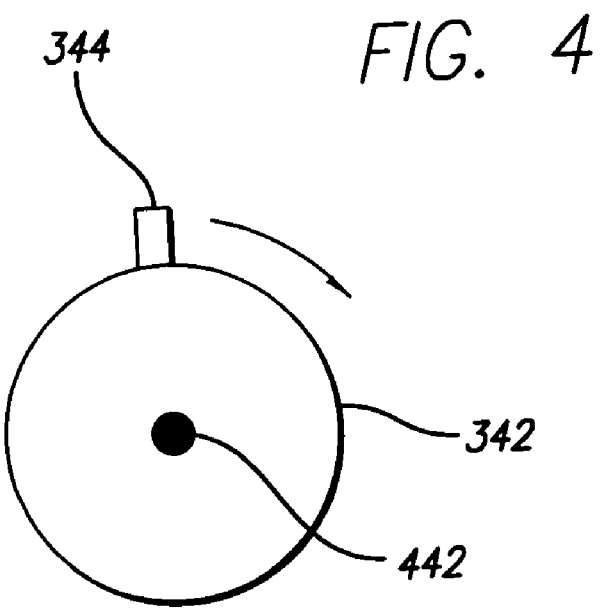
FIG. 4 illustrates a catheter having a data-transmission circuit and a transducer attached thereto, said transducer being adapted for rotation.

In another embodiment of the present the transducer is further adapted to rotate. Specifically, as shown in FIG. 4, a transducer 344 is attached to the distal end of a catheter 342 having a data-transmission circuit 442. In this embodiment of the present invention, the transducer 344 is adapted to rotate around the catheter 342 and receive blood-vessel data from a variety of angular positions, or rotational orientations. In one embodiment of the present invention, the transducer is adapted to start at a particular rotational orientation and rotate (and acquire blood-vessel data) in response (either directly or indirectly) to the transmission of probe-triggering data (e.g., by the data-gathering device). Such an embodiment allows the data-gathering device to be synchronized with the rotational orientation of the transducer.

In another embodiment of the present invention, the transducer is adapted to continuously rotate and continuously gather blood-vessel data. In this embodiment, the data-gathering device may be adapted to identify at least one rotational orientation of the transducer (e.g., a starting rotational orientation). This is because the data-gathering device needs to understand the rotational orientation of the blood-vessel data being acquired. One method of doing this is to start acquiring data when the transducer is in a known rotational orientation (e.g., a starting rotational orientation). Thus, for example, if the transducer is adapted to rotate to two-hundred and fifty-six positions per cycle, and the transducer is continuously rotating and acquiring data, then the data-gathering device may be adapted to identify when the transducer is rotationally oriented in its "starting position," and gather the next two-hundred and fifty-six items of blood-vessel data.

Figure 5:
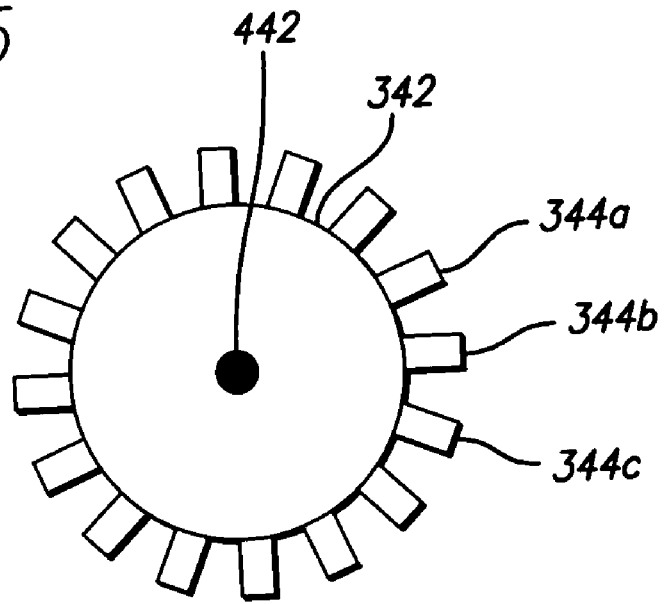
FIG. 5 illustrates a catheter having a data-transmission circuit and a plurality of transducers attached thereto.

In another embodiment of the present invention, a plurality of transducers are located around a catheter. Specifically, as shown in FIG. 5, a plurality of transducers (e.g., 344a, 344b, 344c, etc.) are circumferentially spaced around the distal end of a catheter 342. This allows multiple items of blood-vessel data to be transmitted via the data-transmission circuit 442 (either serially or in parallel). It further eliminates the need for each transducer to rotate. It should be appreciated that the number of transducers depicted in FIG. 5 is not intended to limit the present invention, but is merely provided to identify the environment in which the present invention may operate. Thus, a data-gathering probe having more or less transducers is within the spirit and scope of the present invention.

In another embodiment of the present invention, the data-gathering system further includes a retraction device. Specifically, as shown in FIG. 1, a retraction device 120 is attached to the data-gathering device 110 and adapted to move the data-gathering probe 140 though the blood vessel. It should be appreciated that the data-gathering probe 140, which is physically connected to the retraction device, may be electrically connected to the data-gathering device 110 either directly (not shown) or indirectly (e.g., via the retraction device 120).

In one embodiment of the present invention, the retraction device 120 is further adapted to move the data-gathering probe 140 through the blood vessel at a substantially stead speed. This allows, for example, the data-gathering device 110 to image a blood vessel section (either in two-dimensional or three-dimensional form). Specifically, by acquiring blood-vessel data during intervals that correspond to cyclical portions of heartbeat data and knowing the linear rate at which this data is being acquired (e.g., by providing the speed to, or receiving it from, the data-gathering device), the blood vessel can effectively be recreated or imaged.

It should be appreciated that blood-vessel data can be used in a number of application including, but not limited to, diagnosing and/or treating patients. For example, blood-vessel data can be used to identify and/or image blood vessel boarders or boundaries, as provided by U.S. Provisional Application No., 60/406,184, 60/406,234 and 60/406,185, all of which were filed Aug. 26, 2002, and by U.S. Pat. No. 6,381,350, which issued Apr. 30, 2002, and are incorporated herein, in their entirety, by reference. Another use for blood-vessel data is for classifying and/or imaging vascular plaque, as provided by U.S. Provisional Application No., 60/406,254 and 60/406,148, which were filed Aug. 26, 2002, and by U.S. Pat. No. 6,200,268, which issued Mar. 13, 2001, and are incorporated herein, in their entirety, by reference.

Having thus described a preferred embodiment of a system and method of substantially synchronizing the acquisition of blood-vessel data to an identifiable portion of heartbeat data, it should be apparent to those skilled in the art that certain advantages of the system have been achieved. It should also be appreciated that various modifications, adaptations, and alternative embodiments thereof may be made within the scope and spirit of the present invention. For example, a computing device could be adapted to receive blood-vessel data directly from a data-gathering probe (as oppose to receiving it via an IVUS device). The invention is further defined by the following claims.

What is claimed is:

1. A system for acquiring blood-vessel data, comprising:
a data-gathering probe adapted to acquire blood-vessel data;
a heart-monitoring device adapted to acquire heartbeat data;
a device adapted to move said data-gathering probe continuously through a blood vessel at a substantially constant speed, wherein the data-gathering probe gathers data while being continuously moved at the substantially constant speed; and
a data-gathering device connected to said data-gathering probe and said heart-monitoring device and adapted to:
acquire said heartbeat data;
identify a cyclical portion of said heartbeat data, said cyclical portion being substantially common to multiple sets of heartbeat data;
acquire said blood-vessel data during an interval substantially corresponding to said cyclical portion of said heartbeat data, wherein the data-gathering device is adapted to acquire said blood-vessel data only during the interval while the data-gathering probe is moved continuously through the blood vessel at the substantially constant speed in response to a probe-trigger marking a beginning of the cyclical portion; and
permit analysis of the blood vessel as if the blood vessel was standing still, wherein the analysis of the blood vessel is utilized to classify vascular plaque of the blood vessel.

2. The system of claim 1, further comprising a catheter, said data-gathering probe being attached to a distal end of said catheter.

3. The system of claim 2, wherein said data-gathering probe comprises a plurality of transducers spaced circumferentially around said distal end of said catheter and adapted to receive at least said blood-vessel data.

4. The system of claim 2, wherein said data-gathering probe further comprises at least one transducer adapted to rotate and receive at least said blood-vessel data.

5. The system of claim 4, wherein said data-gathering device is further adapted to start acquiring said blood-vessel data when said at least one transducer is rotationally oriented in a predetermined position.

6. The system of claim 1, wherein said heart-monitoring device comprises an electrocardiograph (EKG) device.

7. The system of claim 1, wherein said data-gathering device comprises a programmable computing device.

8. The system of claim 7, wherein said data-gathering device further comprises an intra-vascular ultrasound (IVUS) device.

9. The system of claim 1, wherein said data-gathering device comprises an intra-vascular ultrasound (IVUS) device.

10. The system of claim 1, wherein the device adapted to move said data-gathering probe through a blood vessel comprises a retraction device.

11. A system for acquiring blood-vessel data, comprising:
a computing device adapted to be connected to a data-gathering probe and a heart-monitoring device;
a device adapted to move said data-gathering probe through a blood vessel continuously at a substantially constant speed, wherein the data-gathering probe gathers data while being moved at the substantially constant speed; and
computer code stored on a non-transitory computer readable medium configured to cause said computing device to:
acquire heartbeat data from said heart-monitoring device;
acquire blood-vessel data while the data-gathering probe is continuously moved through the blood vessel at the substantially constant speed during an interval substantially corresponding to a cyclical portion of said heartbeat data, said cyclical portion being a commonly reoccurring portion of said heartbeat data, wherein the computing device is adapted to acquire said blood-vessel data only during the interval in response to a probe-trigger marking a beginning of the cyclical portion; and
permit analysis of the blood vessel as if the blood vessel was standing.

12. The system of claim 11, wherein said computing device is further adapted to be connected to said data-gathering probe via an intra-vascular ultrasound (IVUS) device.

13. The system of claim 11, wherein said data-gathering probe is disposed on a distal end of a catheter having at least one transducer via an intravascular device.

14. The system of claim 11, wherein said heart monitoring device comprises an electrocardiograph (EKG) device.

15. The system of claim 11, wherein said computer code is further adapted to transmit probe-triggering data during said interval, said probe-triggering data signifying a desire to acquire said blood-vessel data from said data-gathering probe.

16. The system of claim 11, wherein said computer code is further adapted to identify a rotational orientation of said data gathering probe.

17. The system of claim 11, wherein said computer code is further adapted to identify a speed at which said retraction device is moving said data-gathering probe through said blood-vessel.

18. The system of claim 11, wherein the device adapted to move said at least one data-gathering probe through a blood vessel comprises a retraction device.

19. The system of claim 11, wherein said data-gathering probe comprises at least one transducer.

20. A method of acquiring blood-vessel data from a patient, comprising:
inserting a data-gathering probe into a blood vessel of a patient;
connecting said data-gathering probe to a data-gathering device;
attaching at least one heart-monitoring device to said patient;
connecting said at least one heart-monitoring device to said data-gathering device;
moving said data-gathering probe through said blood vessel continuously at a substantially constant speed, wherein said data-gathering probe gathers data while being moved at the substantially constant speed;
acquiring heartbeat data from said at least one heart-monitoring device;

identifying a cyclical portion of said heartbeat data that is substantially common to more than one set of heartbeat data;

acquiring blood-vessel data from said data-gathering probe during an interval that substantially corresponds to said cyclical portion of said heartbeat data, wherein the acquiring blood-vessel data step is performed only while the data-gathering probe is continuously moved through the blood vessel at the substantially constant speed and during the interval in response to a probe-trigger marking a beginning of the cyclical portion; and analyzing the blood vessel as if the blood vessel was standing still.

21. The method of claim 20, wherein said step of inserting a data-gathering probe into a blood vessel further comprises inserting a catheter into said blood vessel.

22. The method of claim 21, wherein said step of connecting said data-gathering probe to a data-gathering device further comprises connecting said catheter to an intra-vascular ultrasound (IVUS) device.

23. The method of claim 22, wherein said step of attaching at least one heart-monitoring device further comprises attaching an electrocardiograph (EKG) device to said patient.

24. The method of claim 23, wherein said step of connecting said at least one heart-monitoring device to said data-gathering device further comprises connecting said EKG device to a computing device connected to said IVUS device.

25. The method of claim 20, wherein said step of acquiring blood-vessel data further comprises receiving blood-vessel data from said data-gathering probe during said interval.

26. The method of claim 20, wherein said step of acquiring blood-vessel data further comprises continuously receiving blood-vessel data from said data-gathering probe and storing blood-vessel data during said interval.

27. The method of claim 20, further comprising the step of rotating at least a portion of said data-gathering probe during the acquisition of said blood-vessel data.

28. The method of claim 27, wherein said step of acquiring blood-vessel data further comprises transmitting probe-triggering data at the beginning of said interval and receiving blood-vessel data from said data-gathering probe in response thereto.

29. The method of claim 27, wherein said step of acquiring blood-vessel data further comprises acquiring blood-vessel data during said interval and when said at least a portion of said data-gathering probe is rotationally oriented in a predetermined position.

30. A method of acquiring blood-vessel data, comprising:
inserting a data-gathering probe into a blood vessel of a patient;
connecting said data-gathering probe to a data-gathering device;
attaching at least one heart-monitoring device to said patient;
connecting said at least one heart-monitoring device to said data-gathering device;
moving said data-gathering probe through said blood vessel continuously at a substantially constant speed, wherein the data-gathering probe gathers data while being moved at the substantially constant speed;

acquiring heartbeat data from said at least one heart-monitoring device over multiple heart cycles;
identifying a cyclical portion of said heartbeat data; and
substantially synchronizing acquiring multiple sets of blood-vessel data to the cyclical portion of the heartbeat data, wherein the acquiring is performed while the data-gathering probe is continuously moved through the blood vessel at the substantially constant speed only during an interval in response to a probe-trigger marking a beginning of the cyclical portion.

31. The method of claim 30, wherein said step of inserting a data-gathering probe further comprises inserting a catheter having at least one transducer into said blood vessel of said patient.

32. The method of claim 31, further comprising the step of identifying a rotational orientation of said at least one transducer.

33. The method of claim 32, wherein said step of substantially synchronizing the acquisition of multiple sets of blood-vessel data to cyclical portions of said multiple sets of heartbeat data further comprises commencing the acquisition of each set of blood-vessel data when said transducer is rotationally oriented in a particular position.

34. The method of claim 30, wherein said step of connecting said data-gathering probe to a data-gathering device further comprises connecting a catheter having at least one transducer to an intra-vascular ultrasound (IVUS) device.

35. The method of claim 30, wherein said step of connecting said at least one heart-monitoring device to said data-gathering device further comprises connecting at least one electrocardiograph (EKG) to a computing device, said computing device further being connected to an intra-vascular ultrasound (IVUS) device.

36. The method of claim 30, further comprising tracking the movement of said data-gathering probe through said blood vessel.

37. A method for gated acquisition of intra-vascular ultrasound (IVUS) data, comprising the steps of:
monitoring a physiological signal of a patient, where the physiological signal correlates with a cardiac cycle for the patient;
advancing an IVUS catheter to a region of interest within a coronary artery;
moving the catheter continuously at a substantially constant speed;
acquiring data while the catheter is continuously moved at the substantially constant speed, wherein the acquiring is performed only during an interval in response to a probe-trigger marking a particular point in the cardiac cycle; and
analyzing the coronary artery as if the coronary artery was standing still.

38. The method of claim 37, wherein said IVUS catheter further comprises a rotating transducer.

39. The method of claim 37, wherein said IVUS catheter further comprises an array of transducers.

40. The method of claim 37 wherein moving the catheter comprises initiating a pullback of the catheter.

41. The method of claim 37, wherein acquiring data is performed while the catheter is pulled back.

* * * * *